United States Patent
Buhring et al.

(10) Patent No.: US 7,364,863 B2
(45) Date of Patent: Apr. 29, 2008

(54) MONOCLONAL ANTIBODY W8B2 AND METHOD OF USE

(75) Inventors: Hans-Jorg Buhring, Tuebingen (DE); Reiner Lammers, Tuebingen (DE); Wichard Vogel, Herrenberg (DE)

(73) Assignee: Eberhard-Karls-Universitaet Tuebingen Universitaetsklinikum (DE)

( * ) Notice: Subject to any disclaimer, the term of this patent is extended or adjusted under 35 U.S.C. 154(b) by 8 days.

(21) Appl. No.: 11/077,486

(22) Filed: Mar. 9, 2005

(65) Prior Publication Data

US 2005/0214873 A1  Sep. 29, 2005

Related U.S. Application Data

(63) Continuation of application No. PCT/EP03/09883, filed on Sep. 5, 2003.

(30) Foreign Application Priority Data

Sep. 9, 2002  (DE) ............... 102 42 338

(51) Int. Cl.
  *G01N 33/53*   (2006.01)
  *C12N 5/00*    (2006.01)
  *C07K 16/00*   (2006.01)
  *C12P 21/08*   (2006.01)
(52) U.S. Cl. .................. 435/7.1; 435/396; 530/387.1; 530/388.1
(58) Field of Classification Search .................. None
  See application file for complete search history.

(56) References Cited

U.S. PATENT DOCUMENTS 5,837,539 A   11/1998   Caplan et al.
6,245,898 B1 *  6/2001  Testa et al. ............ 530/388.85
2004/0053343 A1 * 3/2004  Buehring et al. ............ 435/7.2

FOREIGN PATENT DOCUMENTS

WO   WO-92/22584   12/1992

OTHER PUBLICATIONS

Brazelton et al., Science (2000) 290:1775-1779.
Database BIOSIS 'Online!' Nov. 16, 2000, Giesert Christina et al., XP-002277216, Database Accession No. PREV200100322401.
Giesert et al., Annals New York Academy of Sciences (2001) 938:175-183.
Giesert et al., Letter to the Editor, Univ. of Tubingen, Department of Internal Medicine II.
Kohler and Milstein, Nature (1975) 256:495-497.
Kopen et al., PNAS USA (1999) 96:10711-10716.
Kuci et al., Blood (2003) 101:869-876.
Lagasse et al., Nature Medicine (2000) 6:1229-1234.
Vogel et al., Haematologica (2003) 88:126-133.
Woodbury et al., J. Neuroscience Research (2000) 61:364-370.
Wulling et al., Hum. Pathol. (2003) 34:983-993.
Yin et al., Blood (1997) 90:5002-5012.
Yu et al., J. Biol. Chem. (2002) 277:20711-20716.

* cited by examiner

*Primary Examiner*—Michail Belyavskyi
(74) *Attorney, Agent, or Firm*—Klarquist Sparkman, LLP

(57) ABSTRACT

The invention relates to a monoclonal antibody, or fragments thereof, for isolating and/or identifying mesenchymal stem cells. In this connection, the antibody, or fragments thereof, bind to an antigen which is the same as that bound to by an antibody which is produced by the hybridoma cell line W8B2, which was deposited on 14.08.2002 in the DSMZ [German collection of microorganisms and cell cultures] under the number DSM ACC2567.

6 Claims, 1 Drawing Sheet

MONOCLONAL ANTIBODY W8B2 AND METHOD OF USE

CROSS-REFERENCES TO RELATED APPLICATIONS

This application is a continuation of copending International Patent Application PCT/EP03/09883 filed on Sep. 5, 2003 and designating the United States, which was not published under PCT Article 21(2) in English, and claims priority of German patent application DE 102 42 338.5 filed on Sep. 9, 2002, which is incorporated herein by reference.

BACKGROUND OF THE INVENTION

1. Field of the Invention

The present invention relates to a monoclonal antibody for isolating and/or identifying mesenchymal stem cells.

2. Related Prior Art

In addition to stem cells for haematopoietic cells, stem cell-like cells, which constitute precursors of non-haematopoietic tissues, are also present in bone mar-row. These precursors of non-haematopoietic tissues were originally termed, inter alia, tissue culture dish-adherent (plastic-adherent) cells and are more recently being termed either mesenchymal stem cells or bone marrow stroma cells (MSCs).

In addition to their being of interest because of their multipotency in regard to differentiation, these cells are also of interest, for example, for their possible use in cell therapy and gene therapy.

The mesenchyme is the embryonic connective tissue, i.e. it is the multi-potent parental tissue for all forms of connective tissue and supporting tissue, for smooth musculature and for skeletal and cardiac musculature. Mesenchymal stem cells can be obtained and isolated from the bone marrow of adult humans. They are multipotent and contribute to the regeneration of bones, cartilage, ligaments, muscles, fat tissue and stroma.

The antibody W7C5 has been described by Giesert et al., "The mono-clonal antibody W7C5 defines a novel surface antigen on hematopoietic stem cells", Annals of the New York Academy of Sciences 938: 175-183, as being a new marker for haematopoietic stem cells. At the same time, it was also shown in this publication that mesenchymal stem cells also express this marker. More recent studies show that this antibody recognizes the CD109 epitope on $CD34^+$/CD38-stem cell populations.

Lagasse et al., "Purified hematopoietic stem cells can differentiate into hepatocytes in vivo", Nat Med, 11: 1229-1234 (2000), Kopen et al., "Marrow stromal cells migrate throughout forebrain and cerebellum, and they differentiate into astrocytes after injection into neonatal mouse brains", Proceedings of the National Academy of Science USA, 96: 10711-10716 (1999) and Brazelton et al., "From marrow to brain: expression of neuronal phenotypes in adult mice", Science 290: 1775 1779 (2000), showed that mesenchymal stem cells which had been isolated from bone marrow were also able to differentiate into non-mesenchymal cells such as liver cells, neuronal cells and glial cells. In addition to this, it has only recently been shown that mesenchymal stem cells from adult human bone marrow are able to differentiate into neural cells in vitro. Woodbury et al., "Adult rat and human bone marrow stromal cells differentiate into neurons", J. Neurosci. Res. 61: 364 370 (2000), showed that, in the presence of dimethyl sulphoxide (DMSO) and β-mercaptoethanol (BME), it was possible to differentiate mesenchymal stem cells into cells which expressed neurofilament and neurone-specific enolase. Other research groups reported the use of epidermal growth factor and brain-derived neurotrophic factor (BDNF) to differentiate stroma bone marrow cells into nerve cells which expressed nestin, glial fibrillary acidic protein (GFAP) and neurone-specific nuclear protein (Neu N).

The fact that mesenchymal stem cells are also able, under certain conditions, to differentiate into nerve cells means, inter alia, implicate the need to be able to distinguish these mesenchymal stem cells from neuronal precursor cells.

These neuronal precursor cells (=neural progenitor cells, in the following termed NPC) are to be found in the central nervous system. They also express nestin and are able to differentiate into neurones, astrocytes and oligodendrocytes.

Neuronal precursor cells are CD133-positive; this cell surface marker was originally found on haematopoietic stem cells. However, it has recently been shown that this marker is also expressed by nervous tissue and skeletal muscle tissue. For these reasons, this marker is not suitable, on its own, for the purpose of differentiating different stem cells or precursor cells.

Despite the great interest in mesenchymal stem cells, up to now no de-fined protocol for isolating and expanding the cells in culture does exist. Most experiments have been directed towards cultures of mesenchymal stem cells, which latter have been possible to isolate particularly as a result of their adhering firmly to tissue culture dishes.

Since, furthermore, mesenchymal stem cells and, for example, neuronal precursor cells are considered as being homogeneous populations, particularly in regard to their morphology and their phenotype, there is need, for these reasons as well, to be able to distinguish at least between both these stem cells and precursor cells.

U.S. Pat. No. 5,837,539 discloses antibodies which are specific for cell surface determinants on human mesenchymal stem cells. In order to generate these antibodies, mice were immunized for several days with a variety of human bone marrow-derived mesenchymal stem cells.

These antibodies were used, in particular, for differentiating mesenchymal stem cells from haematopoietic cells. In addition to this, it was found that these antibodies also crossreacted with other non-mesenchymal cells.

SUMMARY OF THE INVENTION

Against this background, the object of the present invention is to provide a novel monoclonal antibody which makes it possible to identify, and, where appropriate, separate, mesenchymal stem cells in a stem cell-containing culture.

According to the invention, this object is achieved by means of an anti-body, or a fragment thereof, which binds to the same antigen as an antibody which is produced by the hybridoma cell line W8B2, which was deposited, in accordance with the Budapest Treaty, on 14, Aug. 2002 in the Deutsche Sammlung von Mikroorganismen und Zellkulturen (DSMZ) under the number DSM ACC2567.

The object underlying the invention is thereby fully achieved.

In their own experiments, the inventors were able to demonstrate that it is possible to use the novel antibody according to the invention to selectively isolate and characterize mesenchymal stem cells.

The inventors have also succeeded in using the novel antibody to differentiate mesenchymal stem cells from, for example, neuronal precursor cells outstandingly well.

To the knowledge of the inventors, such an antibody, which can be used to selectively identify mesenchymal stem cells and differentiate them from, in particular, neuronal precursor cells, has not previously been produced.

The inventors were able to produce the antibody using the cell line WERI-RB 1.

This cell line is a cell line which is isolated from a retinoblastoma and which is held, for example, in the German collection of microorganisms and cell cultures under the number DSMZ ACC 90. It was not to be expected, and nor was there any indication to that effect in this field, that it would be possible to use this cell line to generate antibodies for identifying mesenchymal stem cells.

It was surprising in the respect that the W8B2 antibody binds to an antigen which is characteristic for mesenchymal stem cells that it offers an excellent opportunity for selectively identifying mesenchymal stem cells in a sample containing a variety of cell populations. The cell line which is used for the immunization is already differentiated, for which reason it was not to be expected that the antibody according to the invention would recognize a pluripotent mesenchymal stem cell on the basis of its different surface markers.

Within the context of the present invention, it is also possible, instead of using the antibody which is in each case mentioned, to use a fragment of the antibody, without this being expressly mentioned on each occasion. In this connection, "fragment" is understood as meaning any fragment of the antibody which retains the antigen-binding function of the antibody. Examples of such fragments are Fab, F(ab')2, Fv and other fragments, such as CDR (complementarity-determining region, hypervariable region) frag-ments. The said fragments exhibit the binding specificity of the antibody and can also, for example, be prepared recombinantly using known methods.

Kohler and Milstein ("Continuous cultures of fused cells secreting anti-body of predefined specificity", Nature 256: 495 497) described the production of mono-clonal antibodies, by fusing spleen cells from immunized mice with myeloma cells, in 1975. The techniques for preparing monoclonal antibodies, involving chemically selecting the hybridomas which result from such a fusion and subsequently isolating cell clones which secrete individual antibodies, are likewise known within the field.

Another object of the present invention is an antibody, or a fragment thereof, which is produced by the hybridoma cell line W8B2, which was deposited, in accordance with the Budapest Treaty, on 14, Aug. 2002 in the DSMZ under the number DSM ACC2567.

The inventors showed, in their own experiments, that the above-mentioned antibody is specific for mesenchymal stem cells. The inventors furthermore showed, in their own experiments, that it was possible to use the novel antibody to fractionate mesenchymal stem cells which exhibited a known immunophenotype (in each case positive for CD10, CD13, CD61, CD90, CD105 (endoglin)) into subpopulations.

Furthermore, the antibody produced by the hybridoma cell line W8B2 advantageously proved not to be reactive with bone marrow mononuclear cells (BMMNC). This makes it possible for the selection for mesenchymal stem cells to be extremely specific.

The antibody according to the invention now also makes it possible to prepare additional antibodies which bind to the same antigen. With the aid of the antibody according to the invention, it is possible to use well-known methods to isolate the corresponding antigen structure and to develop further monoclonal antibodies against the same antigen structure, with the known methods being used in this respect as well.

Another object of the present invention is a hybridoma cell line which possesses the ability to produce and release these antibodies, and, in particular, to the hybridoma cell line W8B2.

With the novel antibody, the inventors have, for the first time, prepared a monoclonal antibody, as well as a hybridoma cell line which produces and releases this antibody, which makes it possible to selectively recognize mesenchymal stem cells. The antibody consequently constitutes a means, which is thus far unique, for the physician and research worker to detect such cells, on the one hand, and, on the other hand, to manipulate these cells, where appropriate, either using the antibody itself or using reagents which are coupled to it.

A further object of the present invention is a method for isolating and/or identifying mesenchymal stem cells, which method uses an antibody, or a fragment thereof, which binds to the same antigen as does an antibody which is produced by the hybridoma cell line W8B2, which was deposited, in accordance with the Budapest Treaty, on 14, Aug. 2002 in the DSMZ under the number DSM ACC2567.

In this connection, use is made, in particular, of an antibody, or fragments thereof, which is produced by the hybridoma cell line W8B2, which was deposited, in accordance with the Budapest Treaty, on 14, Aug. 2002 in the DSMZ under the number DSM ACC2567.

The inventors have found that it is possible to use the method according to the invention to identify mesenchymal stem cells, in particular, and to differentiate them from neuronal precursor cells, for example.

Another object of the present invention is a method for identifying mesenchymal stem cells using an antibody, which method comprises the following steps:
(a) contacting a sample containing mesenchymal stem cells to the novel monoclonal antibodies, or fragments thereof, and
(b) identifying the cells in the sample which bind the novel monoclonal antibodies, or fragments thereof.

A further object of the present invention is a method for isolating mesenchymal stem cells using an antibody, involving the following steps:
(a) contacting a sample of a cell suspension containing mesenchymal stem cells to the novel monoclonal antibodies, or fragments thereof, and
(b) isolating the cells in the sample which bind the novel monoclonal antibodies or fragments thereof.

The sample can be selected from any source which contains mesenchymal stem cells, that is, for example, a sample from bone marrow, blood or tissue. These cells are obtained using laboratory methods which are known in the prior art.

In this connection, the contacting of a sample of a cell suspension which contains mesenchymal stem cells can be effected in solution, as is the case, for example, when using a flow cytometer (=fluorescence-activated cell sorter (FACS)).

In flow cytometry, cells are loaded with antibodies which are, on the one hand, specific for a surface marker and, on the other hand, coupled to a fluorescent dye. The cells which are marker-positive fluoresce whereas the negative cells remain dark. The proportion of a cell population which is marker-positive can consequently be established. At the same time, a flow cytometer makes it possible to determine the size and granularity of cells.

It is also possible to use a method for separating cells magnetically (MACS, magnetic cell sorting). In this method, the cells are labeled with magnetic beads, whereby these beads can be coupled, for example, to the antibodies.

Furthermore, the contacting can also be performed by immobilizing the monoclonal antibodies on a carrier, as this is the case, for example, in column chromatography.

After the cell suspension has been mixed with the antibodies, the cells which express the antigen in question bind the antibodies, whereupon the described method can be used to distinguish and/or isolate these cells from the cells which have not bound any antibodies.

The mesenchymal stem cells which have been isolated and/or identified in this way can be used, for example, for a transplantation which is intended to regenerate bones, cartilage, tendons, muscles, fat tissue or stroma.

The invention also relates to the use of the novel antibody, or a fragment thereof, for isolating and/or identifying mesenchymal stem cells.

The invention also relates to the use of the cell line WERI RB 1 for pre-paring antibodies, or fragments thereof, for isolating and/or identifying mesenchymal stem cells.

Another object of the present invention is a pharmaceutical composition comprising the novel antibody according to the invention, or fragments thereof.

In addition to the one or more antibodies, such a pharmaceutical composition can comprise additional suitable substances such as diluents, solvents, stabilizers, etc. These include, for example, physiological sodium chloride solutions, water, alcohols and other suitable substances which can be found, for example, in A. Kibble, "Handbook of Pharmaceutical Excipients", 3rd ed., 2000, American Pharmaceutical Association and Pharmaceutical Press.

A further object of the present invention is a kit which contains the novel antibody, or fragments thereof.

Other advantages ensue from the attached figures and the description.

It will be understood that the abovementioned features, and the features which are still to be explained below, can be used not only in the combination which is in each case specified but also on their own, or in other combinations, without departing from the scope of the present invention.

Exemplary embodiments are depicted in the attached drawing and are explained in more detail in the description.

DESCRIPTION OF PREFERRED EMBODIMENTS

Figure 1:
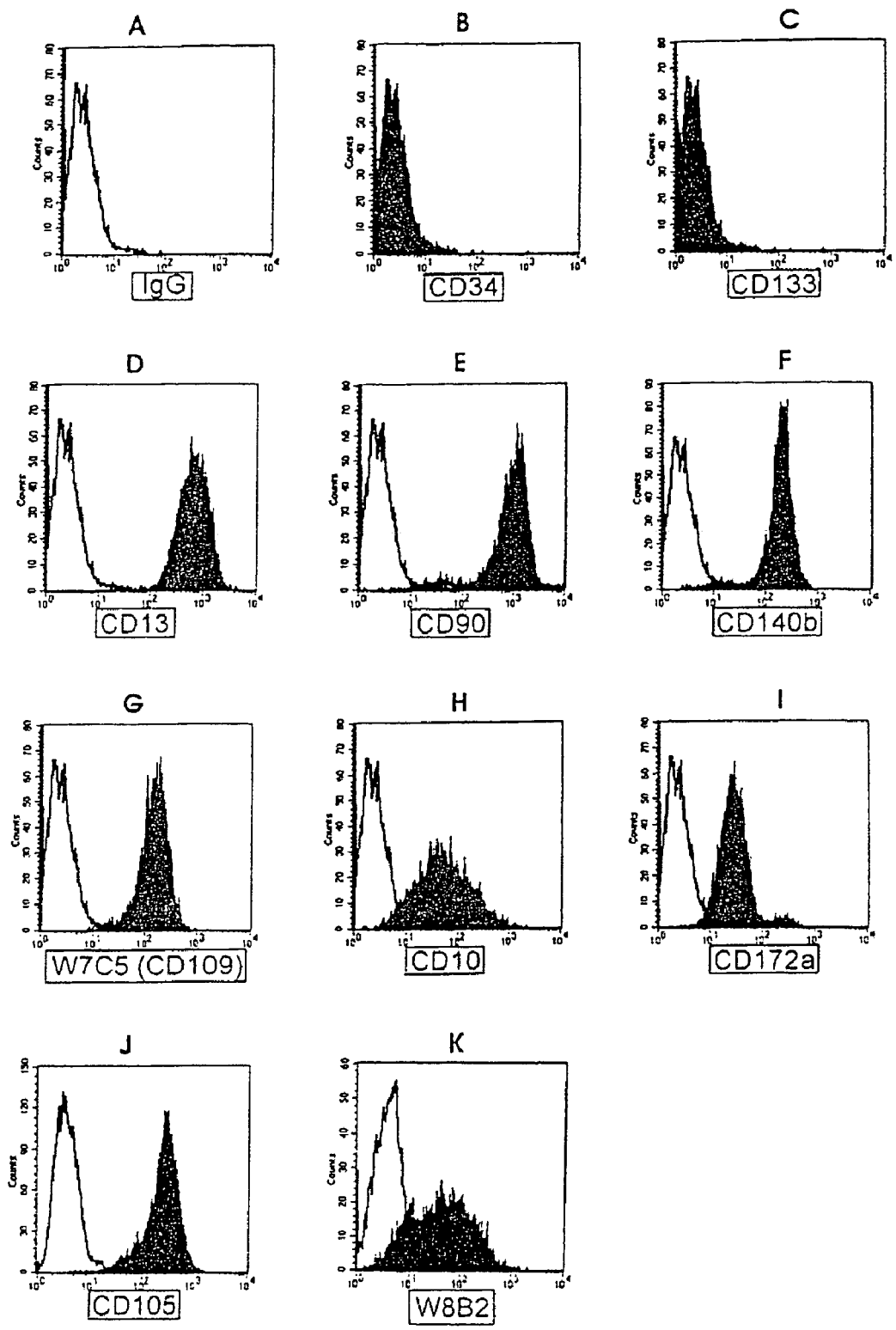
FIG. 1 shows FACS analyses which demonstrate that MSCs express CD13, CD90, CD140B, W7C5 (CD109), CD10, CD172A, CD105 and the novel marker W8B2.

Material and Methods
Isolating and Culturing MSCs:

Mesenchymal stem cells were obtained in two different ways: in one approach, they were isolated by the inventors themselves while, in a second approach, additional mesenchymal stem cells were purchased from the CellSystems company, St. Katharinen, Germany. The mesenchymal stem cells obtained in the two approaches were compared with each other in subsequent studies.

In order to obtain the mesenchymal stem cells, pelvic region bone mar-row cells were obtained from voluntary donors (n=10). The bone marrow cells were separated by density gradient centrifugation and the mesenchymal stem cells were isolated from the interphase (Biocoll separating solution, 1.077 g/ml, Biochrom KG, Berlin, Germany).

The separated cells were cultured in RPMI 1640 medium in the presence of added Glutamax, 1% nonessential amino acids, 1% sodium pyruvate (GIBCOBRL, Paisley, Scotland), 1% penicillin/streptomycin (Biochrom KG) and 10% foetal calf serum (PAA Laboratories, Linz, Austria). At a concentration of $2.0\times10^5$ cells/cm$^2$, the cells were maintained in tissue culture flasks (75 cm$^2$, Cellstar, Frickenhausen, Germany) and incubated at 37° C. in a moistened atmosphere (5% CO2). Two days after the incubation, the nonadhering cells were removed by replacing the medium with new medium. The cells were then released by incubating with 0.25% trypsin/1 mM EDTA at 37° C. for 3 minutes. The mesenchymal stem cells were passaged and subcultured five times. For immunohisto-chemical studies, the first passage of the MSCs was cultured on 8-well slides (Falcon, Heidelberg, Germany) at a density of $1.0\times10^4$ cells/cm$^2$.

The following monoclonal antibodies or antibody conjugates were used for the fluorometric analyses: W8B2, W8C3, W4A5 and W7C5, all of which were obtained from the retinoblastoma cell line WERI RB 1. This cell line can be obtained from the DSMZ under the number ACC90.

Use was also made of the monoclonal antibody 57D2, which was obtained by immunizing mice with the TF 1 erythroleukaemic cell line (DSMZ: ACC334).

CD10 PE, CD13 PE, CD34 PE, CD45 PE, CD56 PE, CD61 PE and CD117 PE (all of which can be obtained from Becton Dickinson, Heidelberg, Germany) were used as antibodies possessing known specificities. PE (phycoerythrin)-conjugated monoclonal antibodies having specificity for CD90, CD140B and CD164 were obtained from PharMingen (San Diego, USA). The anti-nerve growth factor receptor (NGFR) antibody was purchased from Sigma (Munich, Germany). CD133-PE (clone W6B3C1), CD167a (clone 48B3), CD172a-PE (clone SE5A5) and the CD 105-specific monoclonal antibody 43A3 were prepared in the inventors' laboratory. Unconjugated antibodies were stained with isotype-specific, PE-conjugated goat anti-mouse antisera (Southern Biotechnology Associates, Inc., Birmingham, USA).

Staining the Cells and Flow Cytometry

For the cytometric analyses, the trypsin-treated MSCs were incubated, at 4° C. for 20 minutes, with 10 µl of phycoerythrin-conjugated antibodies or 25 µl of culture supernatant in 96 well microtitre plates. Unconjugated monoclonal antibodies were stained, after a washing step in FACS buffer (PBS; 0.5% BSA; 0.1% NaN3), with goat anti-mouse IgG1-PE (1:100) or goat anti-mouse IgG3-PE (1:20) antisera. After a further washing step, the cells were analysed with a flow cytometer (FACSCalibur, Becton Dickinson) using the Cell-Quest software (Becton Dickinson).

For the immunocytochemical analysis of intracellular antigens and ex-tracellular matrix proteins, the mesenchymal stem cells were fixed for 2 minutes with acetone on 8 well chamber slides and labeled for 60 minutes with the primary antibody. They were then stained with Alexa 488-conjugated goat anti-mouse IgG or goat anti-rabbit IgG antisera. For the controls, cells were labeled either with an isotype-appropriate control antibody or with a pre-immune rabbit serum. The fluorescence of the cells was evaluated using a fluorescence microscope (Zeiss, Oberkochen, Germany).

RT PCR Analyses

The total RNA was isolated from cell lysates using the High-Pure RNA Isolation kit (Roche Molecular Biochemicals, Mannheim, Germany) in accordance with the manufacturer's instructions. This protocol includes incubating with DNase in order to digest contaminating DNA. Approximately 1 μg of total RNA was subjected to a 20 μl cDNA synthesis reaction using the random primer: 1$^{st}$ Strand cDNA Synthesis kit for RT PCR (AMV), Roche. 2 μl of the cDNA were used for the PCR amplification. In order to monitor the integrity of the DNA and the efficiency of the cDNA synthesis, 1 μl of the cDNA was amplified using an intron-spanning primer pair for the β2 microglobulin gene.

10 μl of the PCR reaction were analysed on a 3% agarose gel and visu-alized using ethidium bromide.

Results

MSC Immunophenotype

The phenotype of commercially obtainable MSC (2 passages) was com-pared with the phenotype of MSCs which were prepared in the inventors' laboratory (see above). In the latter case, bone marrow cells from healthy donors were cultured, at a density of 2.0×10$^5$ cells/cm$^2$, in tissue culture flasks (75 cm$^2$), in RPMI medium containing 10% foetal calf serum, for from 10 to 14 days. The adhering MSC population which resulted from this culture was heterogeneous and consisted of fibroblast-like cells in addition to round and polygonal cells of different size.

The phenotype of these MSCs was analysed at different passages (passages 15=14 61 days of culture).

Flow-cytometric analyses showed that the MSCs of all the passages, including the commercially obtainable MSCs, expressed CD10, CD13, CD56, CD61, CD90, CD105 (endoglin), CD 140b (PDGF RB), CD 164 and CD 172a (SIRPα) and also the antigens which are defined by the antibodies W8B2 and W7C5 (CD 109) which were prepared in accordance with the invention. However, the MSCs were negative for CD15, CD45, CD34, CD117, CD133 and CD167a.

FIG. 1 depicts selected examples of these analyses. Thus, it can be seen from histograms B and C in FIG. 1 that the mesenchymal stem cells are clearly negative for the markers CD34 and CD133. In most cases, the patterns of expression shown by the commercially obtainable MSCs and the MSCs which were prepared in the inventors' laboratory were identical or at least similar. It can be seen from histograms G and K in FIG. 1 that the mesenchymal stem cells express W7C5 (CD109) and W8B2.

The results of the inventors' investigations are summarized in the following Table 1, in which the antigen expression on mesenchymal stem cells is compared with that on mononuclear cells from the bone marrow of healthy donors.

In the table, − means negative, i.e. no expression on the cells in question, + means positive, i.e. expression on the cells, (+) means positive in at least one analysis, S means little to no detectable expression while P means cell population <5%.

| Antigen/antibody | MSC lab. | MSC comm. | BMMNC |
|---|---|---|---|
| CD13 | + | + | P |
| CD34 | − | − | P |
| CD45 | − | − | + |
| CD56 | S | S | P |
| CD90 | + | + | P |
| CD105 | + | + | P |
| CD117 | − | − | P |
| CD133 | − | − | P |
| CD140B | + | + | P |
| CD164 | + | + | + |
| CD167 | − | S | − |
| CD172a | + | + | + |
| W4A5 | − | − | − |
| W6D3 (CD15) | − | − | + |
| W7C5 (CD109) | + | + | P |
| W8B2 | + | − | − |
| NGFR | (+) | (+) | − |

In addition to this, the inventors showed that antigen expression on MSCs was heterogeneous in dependence on the number of passages. Expression of the W7C5 (CD109) antigen was found to decrease stepwise down to 10% of the original value as the cells went through the first to the fifth passage.

The reactivity of the monoclonal antibody W8B2 with MSCs also de-creased significantly as the number of passages increased. This showed, therefore, the existence of status-specific expression and that the MSC populations were heterogeneous.

In further studies, experiments were carried out to investigate the extent to which the mesenchymal stem cell-specific antibodies W8B2 and W7C5 (CD109) bind to neuronal precursor cells, for example. Neuronal precursor cells which were purchased from the company CellSystems (St. Katharinen, Germany) were used for this purpose. The neuronal precursor cells proved to be clearly negative for the novel antibody W8B2 and the antibody W7C5 (CD 109). Accordingly, the antibody according to the invention is an outstanding agent for distinguishing between, for example, mesenchymal stem cells and neuronal precursor cells.

An immunofluorescence analysis of MSCs which were growing on chamber slides was carried out for the purpose of analysing the expression of intracellular differentiation antigens and extracellular matrix proteins. Unstained cells were used as the negative control. While strong intracellular expression of vimentin was observed in most MSCs, only slight and heterogeneous expression of nestin was observed in small individ-ual cells as well as in larger cells having a polygonal appearance. The MSC cultures also expressed fibronectin. Cytoplasmic Neu-N, β2-chain laminin and the neuronal markers NF, GFAP, β-tubulin and MAP 2 were negative.

mRNA Expression in MSCs

The expression of nestin, MAP 2, neurofilaments, GFAP and β2-chain laminin mRNA was analysed using reverse transcriptase PCR (RT PCR). In agreement with the immunophenotypic analyses, nestin and vimentin mRNA were detected. In addition to this, expression of β2 chain laminin mRNA was also observed. As expected, no neurofilaments, GFAP or MAP-2 mRNA were found in mesenchymal stem cells.

SUMMARY

The studies carried out by the inventors demonstrated that MSCs were typically negative for the following antigens: CD45, CD34 and CD133. The MSCs were positive for CD10, CD13, CD61, CD90 and CD105 (endoglin). This immunophenotype remains consistent over several culture passages and is in agreement with other published data. In addition to this, the inventors showed, for the first time, that MSCs also express CD140b (PDGF RB), CD164 and CD172a (SIRPα). Furthermore, the novel antibody W8B2, which does not react with BMMNC, was able to fractionate the MSC cultures into subpopulations. In addition, it was demonstrated that the stem cell antibody W7C5 (CD109) defines an antigen whose intensity depends on the number of passages of the MSC cultures. As is known, MSCs lose the surface antigens SH3, ICAM 1 and integrinβ1 after culturing of primary cells and lower their production of extracellular matrix molecules. By contrast, after culturing of the primary bone marrow cells, the antigen W8B2 was upregulated in the first-passage MSCs and then downregulated after several further passages. For these reasons, these molecules may play an important role with regard to the proliferation potential or differentiation potential of MSCs. In addition to this, MSCs were also positive for vimentin and fibronectin.

The invention claimed is:

1. An isolated monoclonal antibody, or antigen-binding fragment thereof wherein the monoclonal antibody is produced by the hybridoma cell line W8B2, which was deposited, in accordance with the Budapest Treaty, on 14.08.2002 in the DSMZ under the number DSM ACC2567.

2. A hybridoma cell line which produces the monoclonal antibody according claim 1.

3. Method for isolating and/or identifying mesenchymal stem cells using an antibody, comprising the following steps:

(a) contacting a sample of a cell suspension containing mesenchymal stem cells to a monoclonal antibody according to claim 1, or an antigen-binding fragment thereof, and (b) identifying the cells in the sample which bind the monoclonal antibody, or antigen-binding fragment thereof, thereby isolating and/or identifying mesenchymal stem cells.

4. Pharmaceutical composition comprising the antibody, or antigen-binding fragment thereof, according to claim 1.

5. Kit containing the monoclonal antibody, or antigen-binding fragment thereof, according to claim 1.

6. A method for producing a monoclonal antibody, comprising (a) culturing the hybridoma cell line according to claim 1 in vitro; and (b) isolating monoclonal antibodies produced by the hybridoma cell line.

* * * * *